United States Patent [19]

Kablaoui

[11] 3,998,861
[45] Dec. 21, 1976

[54] PREPARATION OF OMEGA-CARBOXYALKANOHYDROXAMIC ACIDS

[75] Inventor: Mahmoud S. Kablaoui, Wappingers Falls, N.Y.

[73] Assignee: Texaco Inc., New York, N.Y.

[22] Filed: June 23, 1975

[21] Appl. No.: 589,330

[52] U.S. Cl. .................. 260/404; 260/534 M; 260/586 R

[51] Int. Cl.² ............ C08K 5/29; C08K 5/33; C07C 101/30

[58] Field of Search .......... 260/404, 586 R, 534 M

[56] References Cited

UNITED STATES PATENTS

| | | | |
|---|---|---|---|
| 3,076,026 | 1/1963 | White | 260/534 M |
| 3,895,071 | 7/1975 | Kablaoui et al. | 260/586 R |
| 3,917,660 | 11/1975 | Sasaki et al. | 260/404 |
| 3,929,845 | 12/1975 | Duranleau et al. | 260/404 |
| 3,933,872 | 1/1976 | Hartlage | 260/404 |

OTHER PUBLICATIONS

Matlack, A. S. et al. "Cleavage of 2–Nitrocyclohexanone by Base" J. Org. Chem. 32, (June 1967), pp. 1995–1996.

*Primary Examiner*—Helen M. McCarthy
*Attorney, Agent, or Firm*—T. H. Whaley; C. G. Ries; George J. Darsa

[57] ABSTRACT

A method of preparing omega-carboxyalkanohydroxamic acids is provided by contacting an ammonium, Group IA or Group IIA metal salt of a nitrocycloalkanone with an acidic mineral acid salt in a carboxylic acid solvent.

18 Claims, No Drawings

1

PREPARATION OF OMEGA-CARBOXYALKANOHYDROXAMIC ACIDS

BACKGROUND OF THE INVENTION

This invention relates to a novel method of preparing omega-carboxyalkanohydroxamic acids and particularly to the preparation of omega-carboxyalkanohydroxamic acids from salts of nitrocycloalkanones.

Carboxyalkanohydroxamic acids can be prepared by reacting an omega-dicarboxylic acid with hydroxylamine hydrochloride. The reaction product resulting from this method, however, provides a mixture of unreacted omega-dicarboxylic acid, omega-dihydroxamic acids and the desired carboxyalkanohydroxamic acid. The mixture of products and reactants obtained by such a method renders it difficult and costly to recover the desired product even when complicated purification steps are employed. In the instance where a mixture of carboxyalkanohydroxamic acids is the desired product and preparation of the same is undertaken employing a mixture of omega-dicarboxylic acids, separation and recovery of desired product is extremely difficult. We have now found a method whereby a range of individual or mixtures of omegacarboxyalkanohydroxamic acids can be produced in exceptionally good yields and in high purities.

SUMMARY OF THE INVENTION

Broadly, this invention contemplates a method of preparing an omega-carboxyalkanohydroxamic acid which comprises contacting an ammonium, Group IA or Group IIA metal salt of a cyclic alpha-nitroketone with an acidic mineral acid salt in the presence of a carboxylic acid solvent.

In accordance with this invention the salt of the cyclic alpha-nitroketone converted to the omega-acid corresponds to the formula:

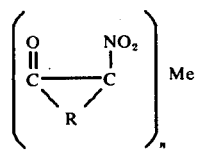

where R is a polymethylene radical of from 1 to 22 carbon atoms or a substituted polymethylene radical of 2 to 22 carbons containing one or more substituents selected from the group consisting of alkyl or aryl and where Me is NH$_4$, a Group IA metal or a Group IIA metal and where n is 1 or 2. Illustrative of the Group IA metals are lithium, sodium and potassium and of the Group IIA metals we mention magnesium, calcium, strontium and barium. The preferred nitroketone salts are those of ammonium, sodium, calcium and magnesium.

By the method of this invention the salt of the cyclic nitroketone is converted to an omega-acid of the formula:

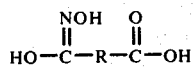

where R is as heretofore defined. It will be appreciated that the diacid is formed by a method whereby the salt of the nitroketone is transformed to the omega-acid through conversion and cleavage. Illustrative of the diacids prepared by the instant method we mention omega-carboxypentanohydroxamic acid, omega-carboxy-3-methylpentanohydroxamic acid, omega-carboxyhexanohydroxamic acid, omega-carboxyheptanohydroxamic acid, omega-carboxydecanohydroxamic acid, omega-carboxydodecanohydroxamic acid, omega-carboxytetradecanohydroxamic acid, omega-carboxyhexadecanohydroxamic acid and omega-carboxyeicosanohydroxamic acid.

Pursuant to this invention, the diacids are prepared from salts of cyclic alpha-nitroketones corresponding to the formula above and include as starting materials the following ammonium salts: ammonium 2-nitrocyclopentanone, ammonium 2-nitro-3-methylcyclopentanone, ammonium 2-nitrocyclohexanone, ammonium 2-nitrocycloheptanone, ammonium 2-nitrocyclooctanone, ammonium 2-nitrocyclodecanone, ammonium 2-nitrocyclododecanone, ammonium 2-nitrocyclopentadecanone, ammonium 2-nitrocyclohexadecanone, ammonium 2-nitrocycloheptadecanone, and ammonium 2-nitrocycloeicosanone. Mixtures of ammonium salts of cyclic nitroketones can also be employed and provide as product mixtures of the diacids. The corresponding Group IA and IIA metal salts are also contemplated such as sodium 2-nitrocyclopentanone, potassium 2-nitrocyclohexanone, lithium 2-nitrocyclopentanone, magnesium 2-nitrocyclohexanone, calcium 2-nitrocyclooctanone, barium 2-nitrocyclodecanone, strontium 2-nitrocyclododecanone as well as mixtures of Group IA or Group IIA salts of nitroketones. The half salts of the Group IIA metals are also contemplated by this method.

The salts of the cyclic nitroketones contemplated as starting materials and illustrated above can be prepared from cyclic alkenes corresponding to the formula:

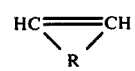

where R is as heretofore defined by simultaneously contacting the cyclic alkene or mixtures of cyclic alkenes with dinitrogen tetroxide and oxygen in a first stage at a temperature between about −40° and 20° C. employing a mole ratio of alkene to dinitrogen tetroxide to oxygen of between about 1:0.5:1 and 1:1.5:30 to form an intermediate peroxy compound and thereafter contacting the intermediate peroxy compound in a second stage with a denitrating agent of the type known to the art such as dimethylformamide, diethylformamide, dimethylacetamide, dimethylsulfoxide, diethylsulfoxide, tetramethylurea, tetraethylurea, hexamethylenephosphoramide, 1-methyl-2-pyrrolidinone, 1-ethyl-2-pyrrolidinone, 1-isobutyl-2-pyrrolidinone and 1,3-dimethyl-2-pyrrolidinone. The contacting with a denitrating agent is undertaken under conditions of agitation and at a temperature of between about −60 and 70° C., preferably 0° to 40° C. using a mole ratio of denitrating agent to peroxy compound of about 1:1 to about 20:1 to form the cyclic nitroalkanone. Alternatively, stages one and two can be undertaken simultaneously to form the cyclic nitroalkanone. To promote the contact of the reactants in the individual or combined stages, an inert liquid diluent having a boiling point between about 30° and 100° C. is employed such as n-hexane, n-heptane, carbon tetrachloride and diethylether. The cyclic nitroketone product can be recovered by standard recovery procedures, for example by filtration of the solids after the addition to the reaction mixture to water or by distillation. The nitroketone is converted to the designated salt by contacting the cyclic nitroketone with from about 1 to about 10 moles of ammonia, a Group IA metal hydroxide or a Group IIA metal oxide or hydroxide per mole of nitroketone at a temperature of about −10° to 30° C.

In one embodiment, the method of this invention comprises heating the salt of the cyclic nitroketone as heretofore described at a temperature of from about 60° to 200° C., preferably from about 75° to 130° C., with an acidic mineral acid salt in the presence of a monocarboxylic acid as solvent. Acidic mineral acid salts contemplated herein include the ammonium chloride, ammonium nitrate, ammonium sulfate, ammonium hydrogen sulfate, ammonium phosphate, aluminum nitrate, aluminum sulfate, ferric chloride, cupric nitrate, zinc sulfate and calcium nitrate. The acidic salts mentioned above form a group which enables the method to form the desired diacid in high yields. Other salts such as calcium chloride and calcium sulfate do not function in the same manner and reactions employing the same do not promote the desired reaction. In highly preferred embodiments, we employ ammonium nitrate or calcium nitrate. The mole ratio of cyclic nitroketone salt to acidic mineral acid salt employed herein can range from about 1:0.01 to 1:2 and preferably from about 1:0.1 to 1:1. It is generally beneficial to conduct the reaction such that the water content is maintained below about three weight percent thereby deterring hydrolysis of the carboxy-hydroxamic acid to a dicarboxylic acid.

As described herein, the conversion and transformation of the salt of the nitroketone to the omega-carboxyalkanohydroxamic acid is conducted in the presence of a monocarboxylic acid suitably having from 1 to 16 carbon atoms, as for example formic acid, acetic acid, propionic acid, isobutanoic acid, pentanoic acid, hexanoic acid, octanoic acid, decanoic acid, undecanoic acid, dodecanoic acid and hexadecanoic acid and we prefer to employ carboxylic acids having from 1 to 6 carbon atoms, such as formic, acetic or propionic acids. A particularly preferred acid is acetic acid. The carboxylic acid solvent assists in solubilizing the salt of the cyclic nitroketone thereby ensuring a good contact between the reactants. The carboxylic acid solvent is generally employed in our method in a mole ratio of salt of cyclic nitroketone to solvent of about 1:1 to 1:100, preferably about 1:4 to 1:40. The use of the solvent contributes to improved yields of the diacid and permits the reaction to be substantially completed in from about one-quarter to about 3 hours, although longer reaction times may be employed. At the completion of the conversion and cleavage reaction, the diacid can be recovered by, for example filtration of the product after the addition of the reaction mixture to water or by distillation.

In a particularly preferred embodiment of this invention, a method is contemplated for preparing an omega-carboxyalkanohydroxamic acid wherein a cyclic alkene or a mixture of cyclic alkenes having from 3 to 24 carbons is initially nitrooxidized and denitrated as described above with dinitrogen tetroxide, oxygen and a denitrating agent to form a mixture of the cyclic nitroketone and denitrating agent along with by-product nitric acid and the mixture is thereafter contacted with about 2 to about 10, preferably 2 to 2.5 moles of ammonia, Group IA metal hydroxide or Group IIA metal oxide or hydroxide per mole of cyclic nitroketone at a temperature of about −10° to 30° C. In the course of contacting the crude composition with the basic materials. such as ammonia or calcium oxide, nitric acid is converted to the corresponding nitrate salt, such as ammonium nitrate or calcium nitrate, and the cyclic nitroketone is converted to its salt, such as the ammonium or calcium salt of the cyclic nitroketone. The salts of the nitroketone and nitric acid are insoluble in the mixture and can be easily separated therefrom, if desired, employing any well-known technique, as for example by filtration, centrifugation, decantation, etc. The filtrate, if separated from the insoluble salts, comprises the denitrating agent, inert diluent if employed and by-products such as nitronitrates and nitroalcohols, each of which are soluble and do not react with ammonia or calcium oxide. To the salts of the cyclic nitroketone and nitric acid, there is introduced a monocarboxylic acid of the type described above an amount of about 1 to 100 moles, preferably 4 to 40 moles, of carboxylic acid per mole of cyclic nitroketone salt and the reaction mixture is heated as previously described thereby cleaving and converting the salt of the nitroketone to an omega-carboxyalkanohydroxamic acid. At the completion of the reaction, the diacid can be recovered by extraction with an inert organic solvent followed by stripping of the solvent. Any organic solvent which does not react with the acid product and in which the product is soluble can be employed. Preferably, the solvent possesses a boiling point of between 30° and 120° C. as for example ethylether, benzene, n-hexane, n-heptane and carbon tetrachloride.

By the instant method, salts of cyclic nitroketones can be selectively converted to omega-carboxyalkanohydroxamic acids and at high conversions. The diacids prepared according to this invention are useful as chemical intermediates and intermediates in the synthesis of fuels and lubricant additives.

In order to more fully illustrate the nature of this invention and the manner of practicing the same, the following examples are presented.

EXAMPLE I

Into a 200 milliliter flask equipped with a gas inlet thermometer and condenser, there was charged 16.6 grams (0.1 mole) of cyclododecene, 7.3 grams (0.1 mole) of dimethylformamide and 100 milliliters of carbon tetrachloride. To this solution, maintained at a temperature of 5°–10° C., there was introduced oxygen at the rate of 60 to 80 milliliters per minute and 9.2 grams (0.1 mole) of dinitrogen tetroxide at the rate of 0.05 gram per minute over a period of two hours.

To the above reaction mixture, maintained at 5°–10° C., there was introduced 3.4 gram (0.2 mole) of ammonia as a gas at the rate of 0.12 gram per minute over a period of half hour. The solids composed of ammonium nitrate and the ammonium salt of 2-nitrocyclododecanone were separated from the crude composition by filtration and weighed 29.2 grams. To the solids, there was added 250 milliliters of acetic acid and the mixture was heated at 118° C. for 3 hours. The solution was cooled to room temperature, 400 milliliters of water added thereto, extracted with three 100 milliliter portions of ether, dried and stripped. The recovered residue weighing 20.8 grams (85 percent yield) was identified by infrared and nuclear magnetic resonance to be omega-carboxydodecanohydroxamic acid.

EXAMPLE II

To the apparatus of Example I there was charged 16.6 grams (0.1 mole) of cyclododecene, 7.3 grams (0.1 mole) of dimethyl formamide and 100 milliliters of carbon tetrachloride, and the solution treated with oxygen and 9.2 grams (0.1 mole) of dinitrogen tetroxide as in Example I.

At the end of the dinitrogen tetroxide-oxygen addition period, 5,6 grams (0.1 mole) of calcium oxide was added to the reaction mixture which was maintained at 5°–10° C. After stirring for 15 minutes, the calcium salt of the nitroketone and calcium nitrate were separated by filtration and weighed 30.0 grams. To the solids there was added 250 milliliters of acetic acid and the mixture was heated at 118° C. for 3 hours. The solution was cooled to room temperature, 400 milliliters of water added thereto, extracted with three 100 milliliter portions of ether, dried and stripped. The recovered residue weighed 20.6 grams (84 percent yield) was identified as omega-carboxydodecanohydroxamic acid.

We claim:

1. A method of preparing an omega-carboxyalkanohydroxamic acid which comprises contacting at a temperature of about 60° to 200° C an ammonium, Group IA or Group IIA metal salt of a cyclic alpha-nitroketone with an acidic mineral acid salt which is ammonium chloride, ammonium nitrate, ammonium sulfate, ammonium hydrogen sulfate, aluminum nitrate, aluminum sulfate, ferric chloride, cupric nitrate, zinc sulfate or calcium nitrate, in the presence of a monocarboxylic acid solvent having from 1 to 16 carbon atoms.

2. A method according to claim 1 wherein said contacting is at a temperature of about 75° to 130° C.

3. A method according to claim 1 wherein the mole ratio of said cyclic nitroketone salt to said acidic salt is from about 1:0.01 to 1:2.

4. A method according to claim 1 where the mole ratio of said nitroketone salt to said acid salt is from about 1:0.1 to 1:1.

5. A method according to claim 1 where said salt of the nitroketone corresponds to the formula:

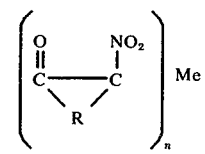

where R is a polymethylene radical of from 1 to 22 carbon atoms or a substituted polymethylene radical of 2 to 22 carbon atoms where Me is $NH_4$, a Group IA metal or a Group IIA metal and where $n$ is 1 or 2.

6. A method according to claim 1 wherein said nitroketone salt is ammonium 2-nitrocyclooctanone.

7. A method according to claim 1 wherein said nitroketone salt is ammonium 2-nitrocyclododecanone.

8. A method according to claim 1 wherein said nitroketone salt is ammonium 2-nitrocyclopentanone.

9. A method according to claim 1 wherein said nitroketone salt is ammonium 2-nitrocyclohexanone.

10. A method according to claim 1 wherein said nitroketone salt is calcium 2-nitrocyclododecanone.

11. A method according to claim 1 wherein said carboxylic acid has from 1 to 16 carbon atoms.

12. A method according to claim 1 wherein said carboxylic acid has from 1 to 6 carbon atoms.

13. A method according to claim 1 wherein said carboxylic acid is acetic acid.

14. A method according to claim 1 wherein said acidic salt is ammonium nitrate.

15. A method according to claim 1 wherein said acid salt is ammonium sulfate.

16. A method according to claim 1 wherein said acid salt is ammonium chloride.

17. A method according to claim 1 wherein said acid salt is ammonium phosphate.

18. A method according to claim 1 wherein said acid salt is calcium nitrate.

* * * * *